United States Patent
Draenert

[11] Patent Number: 5,857,771
[45] Date of Patent: Jan. 12, 1999

[54] APPARATUS FOR REMOVING GAS INCLUSIONS FROM MIXING OF LIQUID AND POWDER COMPONENTS AND FOR VACCUM MIXING SUCH COMPONENTS

[76] Inventor: Klaus Draenert, Gabriel-Max-Str. 3, D-81545 München, Germany

[21] Appl. No.: 974,018
[22] PCT Filed: Aug. 27, 1993
[86] PCT No.: PCT/EP93/02322
§ 371 Date: Feb. 28, 1995
§ 102(e) Date: Feb. 28, 1995
[87] PCT Pub. No.: WO94/05415
PCT Pub. Date: Mar. 17, 1994

Related U.S. Application Data

[63] Continuation of Ser. No. 392,936, Feb. 28, 1995, abandoned.

[30] Foreign Application Priority Data

Aug. 28, 1992 [DE] Germany .......................... 42 28 780.4

[51] Int. Cl.⁶ .................................................... B01F 13/06
[52] U.S. Cl. .......................................... 366/130; 366/139
[58] Field of Search .................................. 366/139, 129, 366/130, 255, 256

[56] References Cited

U.S. PATENT DOCUMENTS

| | | | |
|---|---|---|---|
| 4,758,096 | 7/1988 | Gunnarsson | 366/139 |
| 4,889,432 | 12/1989 | Patterson | 366/139 |
| 4,973,168 | 11/1990 | Chan | 366/139 |
| 5,193,907 | 3/1993 | Faccioli | 366/139 |
| 5,252,301 | 10/1993 | Nilson | 366/139 |
| 5,328,262 | 7/1994 | Lidgren et al. | 366/139 |

FOREIGN PATENT DOCUMENTS

| | | | |
|---|---|---|---|
| WO 87/05492 | 9/1987 | WIPO . | |
| WO 88/03811 | 6/1988 | WIPO . | |
| 88/08327 | 11/1988 | WIPO | 366/139 |
| WO 88/09209 | 12/1988 | WIPO . | |
| WO 90/13264 | 11/1990 | WIPO . | |

*Primary Examiner*—Charles E. Cooley
*Attorney, Agent, or Firm*—Kinney & Lange, P.A.

[57] ABSTRACT

An apparatus and a method of vacuum mixing mixes substances consisting of at least one powder component and at least one liquid component, in particular of bone cement. An evacuatable mixing vessel (1) has a body (4), which is movable within the mixing vessel. The outer circumference of the body (4) and the inner wall of the mixing vessel (1) form an air-tight seal. The inside of the body (4) is provided with an opening which is covered with a filter (9). The filter (9) is designed such that it can be penetrated by air but not by the powder component of the mixture of substances. With the apparatus according to the invention it is possible to produce a mixture of substances which is free of bubbles.

24 Claims, 4 Drawing Sheets

APPARATUS FOR REMOVING GAS INCLUSIONS FROM MIXING OF LIQUID AND POWDER COMPONENTS AND FOR VACCUM MIXING SUCH COMPONENTS

This is a continuation of Ser. No. 08/392,936, filed Feb. 28, 1995 now abandoned, which is a 371 of PCT/EP93/02322, filed Aug. 27, 1993. Priority of the prior application is claimed pursuant to 35 USC § 120.

BACKGROUND OF THE INVENTION

The present invention relates to an apparatus and a process of evacuating and mixing a mixture of substances or a preparation consisting of at least two components. In particular, the present invention relates to an apparatus and a method of degassing a polymer powder and of mixing the polymer powder with a monomer component in a mixing vessel from which the formed mixture of substances which is free of gas can be transferred into an application vessel.

The term "mixing" is generally understood to mean a preparation made up of two different substances. If one of the two substances to be mixed is a fluid and the other a powder, air is usually transferred and introduced into the initial preparation via the powder to which air particles can adhere. As a rule, even more air is introduced into the mixture by the mixing process per se.

On the one hand, the purpose of mixing is to achieve an as homogeneous distribution of the individual components as possible in the mixture, e.g., in order to initiate or promote an as uniform time-dependent chemical reaction as possible between the components, for example the subsequent polymerisation of a two- or multi-component mixture, such as bone cement. On the other hand, a mixture having as few inclusions or occlusions as possible, i.e. no impurities, is to be formed by mixing; for example, as few air inclusions as possible are to be included in the mixture. The less air bubbles are occluded, the higher is for example the strength of the prepared and hardened bone cement.

Several types of mixing apparatus and mixing processes are already known. Mixing can for example be effected by stirring, mingling, rolling, kneading, emulsifying, suspending, centrifuging and/or dissolving or by subjection to ultrasound or vibrators.

Most of the known mixing apparatus and processes have, however, the drawback that impurities, such as air, are introduced into the mixing system during the mixing process and, moreover, that the gas inclusions contained at the beginning and formed during the mixing process, for example due to a chemical reaction of the substances to be mixed, cannot be removed from the mixing system. Attempts have already been made to prevent the formation of gas inclusions by vacuum mixing systems, for example by means of the mixing apparatus described in WO 87/05492 or WO 88/09209 or the system described in the European Patent Application No. 85 11 3151.6.

In the known vacuum mixing apparatus and methods, however, certain air inclusions cannot be completely removed. This is in part due to the fact that the powder component of the mixture of substances to be mixed contains air and must initially be stirred into the liquid component before a vacuum can be applied since otherwise the powder would be sucked off during the evacuation step. Since then a certain reaction, e.g. a polymerisation, between the powder component and the liquid component of the mixture of substances has already started, the air cannot be completely removed any more.

On the other hand, attempts have already been made to evacuate the powder within the packaging, which is a method known for example from the foodstuff industry. Such a method has for example been proposed by Tepic and Perren (Bone cement preparation with vacuum packaged powder to minimize monomer content and increase strength, in: Draenert K. Die Implantatverankerung, Symposiumband, pp. 26, 27, Art and Science, Munich 1985). The disadvantage of this system, however, resides in the fact that all spherical particles of the powder contact each other in a compact structure and are so closely packed that the monomer cannot embed the individual spherules quickly and sufficiently enough to form the desired uniform sphere packing, like exposed aggregate concrete for example; the resulting structure is rather comparable to that of lean concrete.

It is an object of the present invention to provide an apparatus and a process of vacuum mixing a mixture of substances, by means of which the existence of impurities, in particular gas inclusions, in the mixture of substances can be avoided.

SUMMARY OF THE INVENTION

This object is achieved by the apparatus and the method according to the invention. The invention is based on the idea to evacuate the substances to be mixed in a mixing vessel already before the actual mixing step such that the substances to be mixed are degassed already before being mixed, and to subject the substances to be mixed in the same mixing vessel to a vacuum during the actual mixing step to the effect that no air is introduced to the mixture during the actual mixing step either.

According to the invention, the substances to be mixed are preferably a cold-setting two-component system, the first component being for example a polymer powder and the second component a liquid monomer of a conventional, commercially available bone cement. In the following, the invention will basically be described in connection with such two-component systems, but can also be applied to any other mixture of substances.

In case of commercially available bone cements, the powder component is within a bag and the monomer within a small ampoule. According to the invention, the two components can be prepared in a mixing vessel such that first the liquid phase or component is poured into the vessel and the powder phase, such as a bead polymer, is then introduced. Now the powder, whose volume is considerably greater in conventional bone cements, projects out of the liquid phase, e.g. the monomer, by far. In that part of the powder which can immerse into the liquid, part of the air bubbles present between the polymer spherules of the powder are already stripped off. However, during conventional mixing processes, these bubbles are re-captured and re-occluded by the subsequent powder mass. Moreover, in case of conventional mixing processes, the powders, which partially differ considerably with respect to the air volume occluded, often fill in the rest of the mixing vessel and can only be stirred in with great difficulties. As the powder is wetted by the liquid to an increasing extent, the powder may be successfully stirred in; however, a certain period of time, sometimes up to 40 seconds, gets lost; on the other hand, it could be shown that for instance in the case of bone cements the early mixing phase, in particular the first three seconds, is decisive for the elimination of air bubbles from the powder component in order to achieve the elimination of micropores in the finished bone cement which are due to the air inclusions (cf. Draenert, Forschung und Fortbildung in der Chirurgie des Bewegungsapparates 2. Zur Praxis der Zementverankerung, Art and Science, Munich 1988).

According to the invention, the aforementioned object is achieved by evacuating the mixing vessel containing the polymer powder, which projects out of the monomer, already prior to mixing. The mixing vessel preferably is a mixing bowl. Preferably, merely a low negative pressure of about 100 to 300 mbar, preferably of about 250 mbar, is generated during the evacuation, which corresponds to an absolute pressure of about 763 mbar. The polymer powder is degassed by the evacuation. It must be avoided that the polymer powder is sucked off the mixing vessel during the evacuation. This is achieved by providing a piston-shaped body, which is axially movable within the mixing vessel and comprises means sealing the piston with respect to the vessel wall in an essentially vacuum-tight manner such that the piston can nevertheless slide along the vessel wall. The body is formed in such a way that it is air permeable but prevents the polymer powder from penetrating. This can be achieved by a suitable porosity of the material of the piston-shaped body, which is adapted to the particle size of the polymer powder and wherein the diameter of the open pores must be at least slightly smaller than the diameter of the smallest powder particles. The piston can also comprise a larger through-opening and can for example have the form of a ring, the opening being covered by a porous filter, for example a diaphragm or membrane. With regard to the porosity of the filter, the same criteria as mentioned above in connection with the embodiment of a porous piston-shaped body apply to this embodiment. The filter can also be provided such that it seals the piston with respect to the inner wall of the vessel itself.

During the evacuation, the piston-shaped body is sucked into the depth of the mixing vessel by the low pressure generated in the mixing vessel. Hereby the powder is compressed to a fraction of its original volume, preferably to less than three quarters, for example to about two thirds of its original volume. Simultaneously, the monomer from the bottom of the mixing vessel is sucked into the spaces between the spherical particles of the bead polymer powder such that the polymerisation reaction starts within the entire powder volume almost at the same time. The raw mixture thus formed can then very easily be homogeneously mixed by means of a stirrer while a vacuum is also applied, as for example described in WO 87/05492. Preferably, it is first stirred very vigorously for 15 seconds and then for another 15 seconds in laminar layers; thus, mixtures which are free of bubbles can be obtained.

The body which is movable in the mixing vessel is preferably a lamellated body having lamellae sealing the body with respect to the vessel wall, wherein a filter in the form of a filter paper or a textile filter is clamped onto or stretched over the surface of the laminar body facing the powder; it is also possible to use a metal filter stretched over, put onto or attached to the piston. The filter must in any case be formed in such a way that air can be sucked through the filter but not the powder component.

The body can also have the shape of a ring or be equipped with a ring which is movable in the mixing vessel, preferably over its whole length, and over or onto whose end facing the powder a filter is superposed or put, respectively. The end of the ring facing away from the powder can comprise a guiding means for receiving a stirrer, preferably in a press fit, with which stirrer the ring can be moved back and forward along the wall of the vessel. The filter can preferably be such that it can be pierced by the stirrer without parts of the filter falling into the substances to be mixed. For this purpose, the filter can have predetermined rupture points or lines having an interrupted perforation. A strong, tear-resistant filter paper or crepe paper is preferably used as a filter.

At its outer circumference or its lamellae, the annular body preferably comprises a means, for example a retention means, by means of which it can be secured to the edge of the vessel when being pulled out of the vessel. In particular, with this embodiment it is possible to use the mixing apparatus according to the invention as a part of a half-closed or closed system, wherein the raw mixture of powder and monomer is first sealed off by the diaphragm of the filter and the mixture can be prepared after the diaphragm is pierced. The guiding means for the stirrer can be fitted into the central opening of the annular body and can be removed together with the stirrer. Moreover, a central insert or inlay can be provided which comprises openings or slots for the passage of air and carries a microporous filter exhibiting a high tensile strength. The inlay itself can be such a filter. The air-permeable inlay can be an integral part of the guiding means for the stirrer.

The central opening or inner recess of the annular body can have such dimensions that the ring can optionally take up the described filter insert and an adapter in the form of an adapter lamella for a cartridge into which the bone cement can subsequently be injected, as for example described in WO 87/05492. The adapter lamella for the cartridge can be secured to the annular body or piston ring by means of a snap-on or straining ring, after the filter insert has been removed together with the stirring rod.

Over its whole slightly concave surface facing the powder, the ring is porous, the porosity having the aforementioned dimensions. The ring can be a lamellated body having several lamellae for sealing it with respect to the vessel wall and a cylindrical inner ring. The inner ring is provided with one or more channels in such a way that during the evacuation step air can be sucked off the mixture of substances via the porous surface of the piston ring through the channel(s) of the inner ring, even after inserting the filter.

The porosity of the body or filter is adapted to the particle size of the powder component of the mixture of substances such that the body or filter is not permeable to the particles, and is for example 1 to 40 $\mu$m, preferably about 1 to 10 $\mu$m, when mixing conventional bone cements since the smallest particles of the powder component have slightly bigger dimensions. The powder component of the mixture of substances to be mixed preferably consists of PMMA bead polymer, i.e. acrylate or methacrylate prepolymers or derivatives thereof. The liquid monomer phase preferably consists of acrylic or methacrylic acid derivatives, e.g. of methacrylic methylester.

All components of the apparatus according to the invention are preferably made of such materials that they are sterilisable and can immediately be used in the operating theatre.

BRIEF DESCRIPTION OF THE DRAWINGS

The present invention will be illustrated in the following in detail by means of the drawings, in which.

DETAILED DESCRIPTION OF THE PREFERRED EMBODIMENTS

The vacuum mixing apparatus of the invention according to FIG. 1 comprises a bowl-shaped mixing vessel 1 in which the monomer of a commercially available bone cement is poured, into which the powder is dumped subsequently after cutting open the powder bag. The monomer and powder are not depicted in FIG. 1. The front end of a conventional cartridge 2, which can also be used for subsequently applying the bone cement, comprises a body 4 having the form of a lamellated cylinder and being secured to the front end by means of a bayonet catch 3. The lamellated cylinder can be inserted into the vessel 1 by means of the cartridge 2. The outer circumference of the lamellated cylinder 4 is provided with several lamellae 5, 6 and 7. The lamellae are formed such that the body 4 is sealed with respect to the inner wall of the vessel 1. The foremost lamella 7, which faces the bottom of the vessel, is covered by a filter 9, such as filter paper, which is retained in a stretched position by a ring 8 arranged between the lamellae 6 and 7, such as a rubber ring. The front end of the cartridge 2 is provided with an orifice 10 for the subsequent application of the bone cement. The rear end of the cartridge 2 is provided with a cap 11 having a handle 12. The cap 11 is further provided with a vacuum connection 13 which is sealed by means of sealing rings 14. The cap 11 is connected to the cartridge 2 by means of a bayonet catch 15, at least one sealing ring 16 being provided between the cap 11 and the cartridge 2.

At the beginning of the mixing process according to the invention, after pouring in the monomer and subsequently the powder, the body 4 having the shape of a lamellated cylinder is first inserted into the vessel 1 by means of the cartridge 2 until the filter 9 contacts the polymer powder of the bone cement. Subsequently, the cap 11 is secured to the cartridge 2 by means of the bayonet catch 15. The vacuum connection 13 is connected to a vacuum pump (shown schematically) via a tube and the mixing vessel is evacuated by means of the vacuum pump. Due to the sealing by the lamellae 5, 6 and 7 as well as the sealing rings 14 and 16, a low pressure or partial vacuum is applied to the mixing vessel. Preferably, the low pressure is about 250 mbar below atmospheric pressure. To the same extent as the vessel is evacuated and air is sucked off the polymer powder, the body 4 is further advanced by means of the cartridge 2 using the handle 12. The body 4 can be moved towards the bottom of the vessel in less than one second and thus compress the polymer powder, for example to about two thirds of its original volume. Simultaneously, the liquid monomer is sucked into the polymer powder by the evacuation such that almost simultaneously the polymerization reaction between the powder and the monomer is initiated in the entire mixture. After withdrawing the body 4 via the handle 12, the resulting raw mixture can be mixed with a stirrer according to a known method to form a completely homogeneous mixture while preferably again applying a vacuum, as for example disclosed in WO 87/05492.

Figure 1:
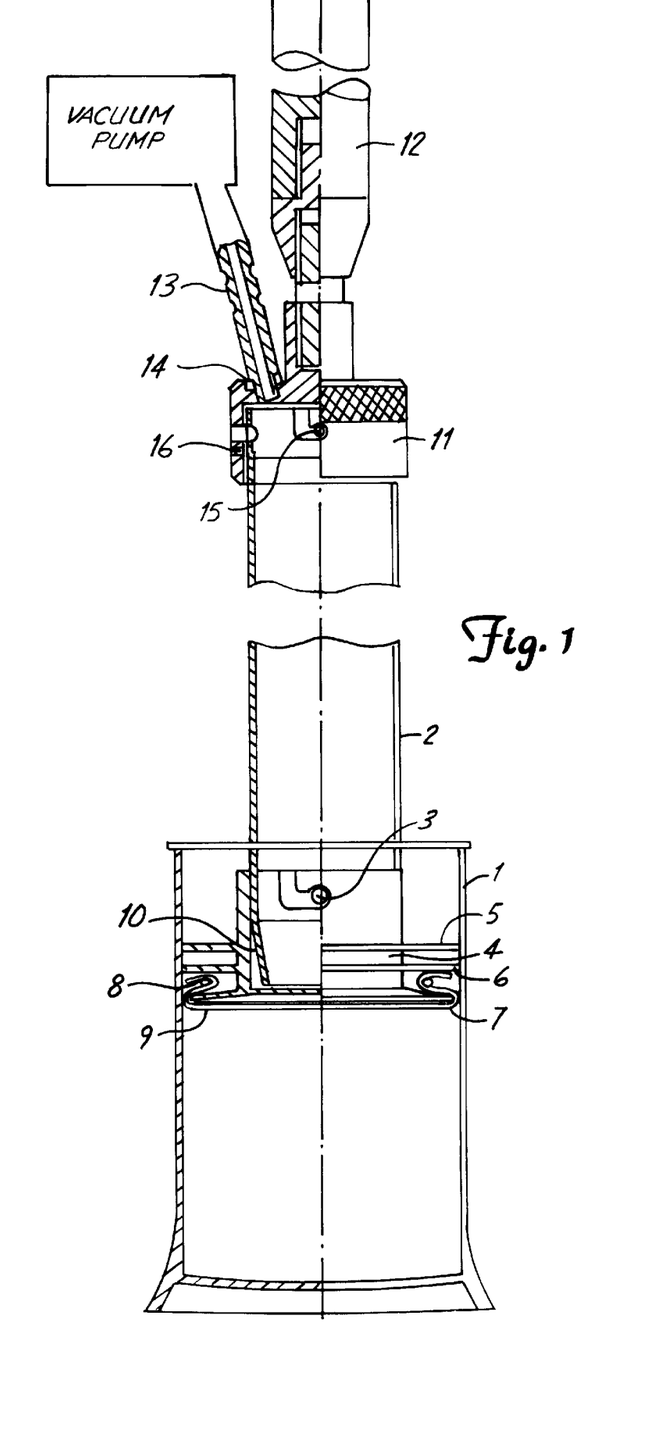
FIG. 1 shows a partial section of a first embodiment of the vacuum mixing apparatus according to the invention.
Figure 2:
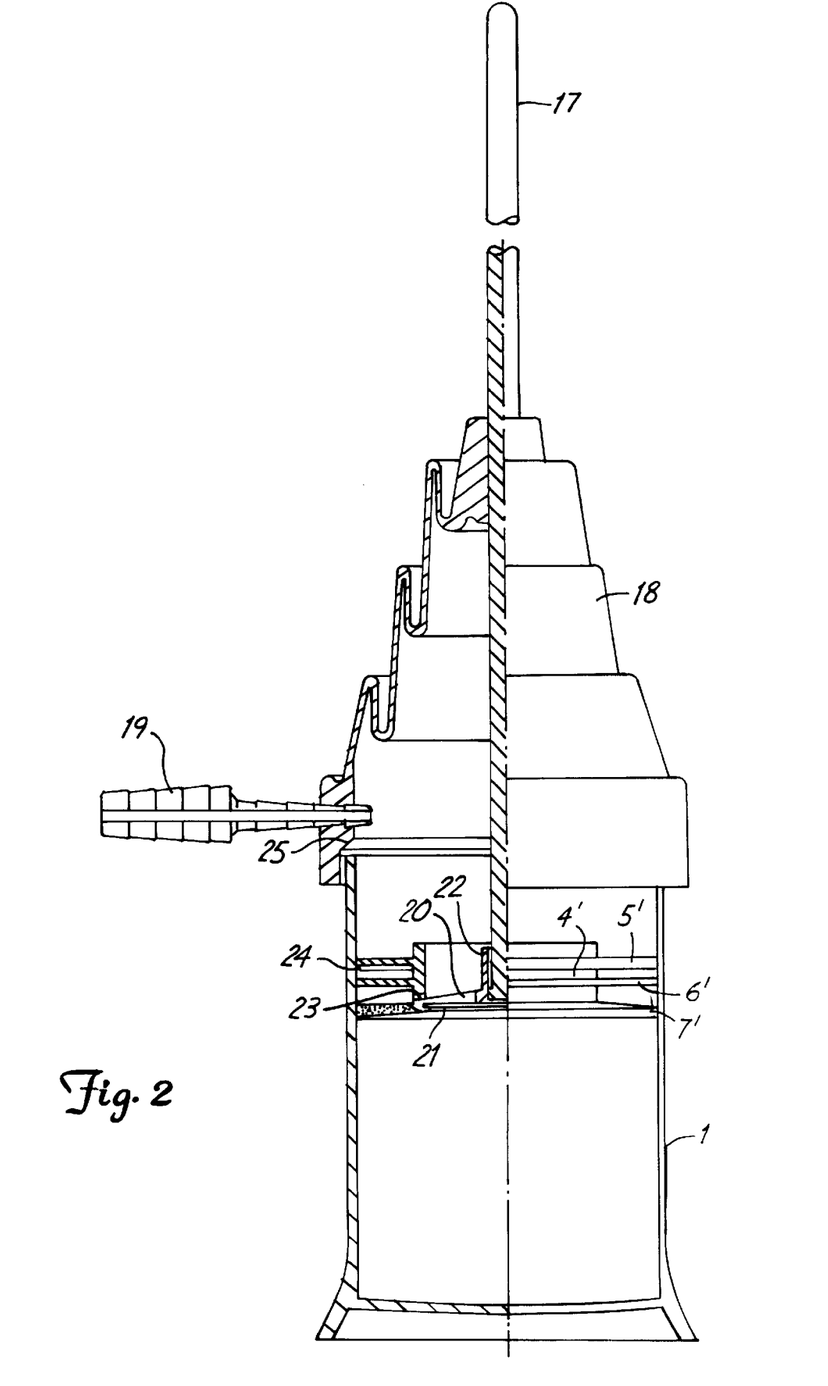
FIG. 2 shows a partial section of a second embodiment of the vacuum mixing apparatus according to the invention.

The vacuum mixing apparatus according to the invention as shown in FIG. 2 can suitably be applied in a half-closed or closed system. The apparatus according to FIG. 2 also comprises a bowl-shaped vessel 1 for taking up the substances to be mixed and a body 4' which is axially movable within the vessel 1 and has the shape of a piston or lamellated cylinder. The lamellated cylinder 4' comprises several lamellae 5', 6' and 7,' and the lamellae 5' and 6' seal it with respect to the inner wall of the vessel 1, just as in the embodiment according to FIG. 1. The foremost lamella 7' facing the bottom of the vessel is perforated and has a predetermined porosity. A stirring rod 17 is inserted into a central filter mounting or a guiding means (which will be described in detail in the following) of the body 4'. Moreover, a vacuum cap 18 resembling that described in WO 88/09209 is provided for sealing the vessel 1. The vacuum cap 18 is provided with a vacuum cannula 19 by means of which a vacuum can be generated via a tube and a vacuum pump (not depicted). The inside of the body 4' is provided with an air-permeable central insert or inlay 20 having for example through openings or slots; into this insert or inlay 20, a filter 21 having the form of a diaphragm or membrane is inserted. The central insert or inlay 20 is securely, however, detachably attached to the body 4' and is for this purpose provided with preformed rupture sites. Moreover, a further insert 22 is provided which forms a press fit with the stirring rod 17 and serves as a guiding means therefor. The inserts 20 and 22 can also be made integrally. One or more channels 23 are provided between the interior space of the body 4' and the space between the lamellae 6' and 7'. The outer edge of the rearmost lamella 5', which faces away from the bottom of the vessel, is provided with a thickening 24. The inside of the vacuum cap 18 is provided with a corresponding recess 25.

When using the apparatus according to the invention as depicted in FIG. 2, after pouring the substances into the vessel 1 as described by means of FIG. 1, the body 4' is moved to the bottom by means of the stirring rod 17 which engages with the central filter mounting. Simultaneously, a low pressure or partial vacuum is generated in the vessel 1, which is sealed by means of the vacuum cap 18, via the vacuum pump connected to the vacuum cannula 19. Thus, air is sucked off the polymer powder. Air is on the one hand sucked off via the porous lamella 7' and the channel(s) 23 towards the vacuum cannula 19 and on the other hand (and mostly) directly via the filter 21 inserted into the central insert 20.

Figure 2A:
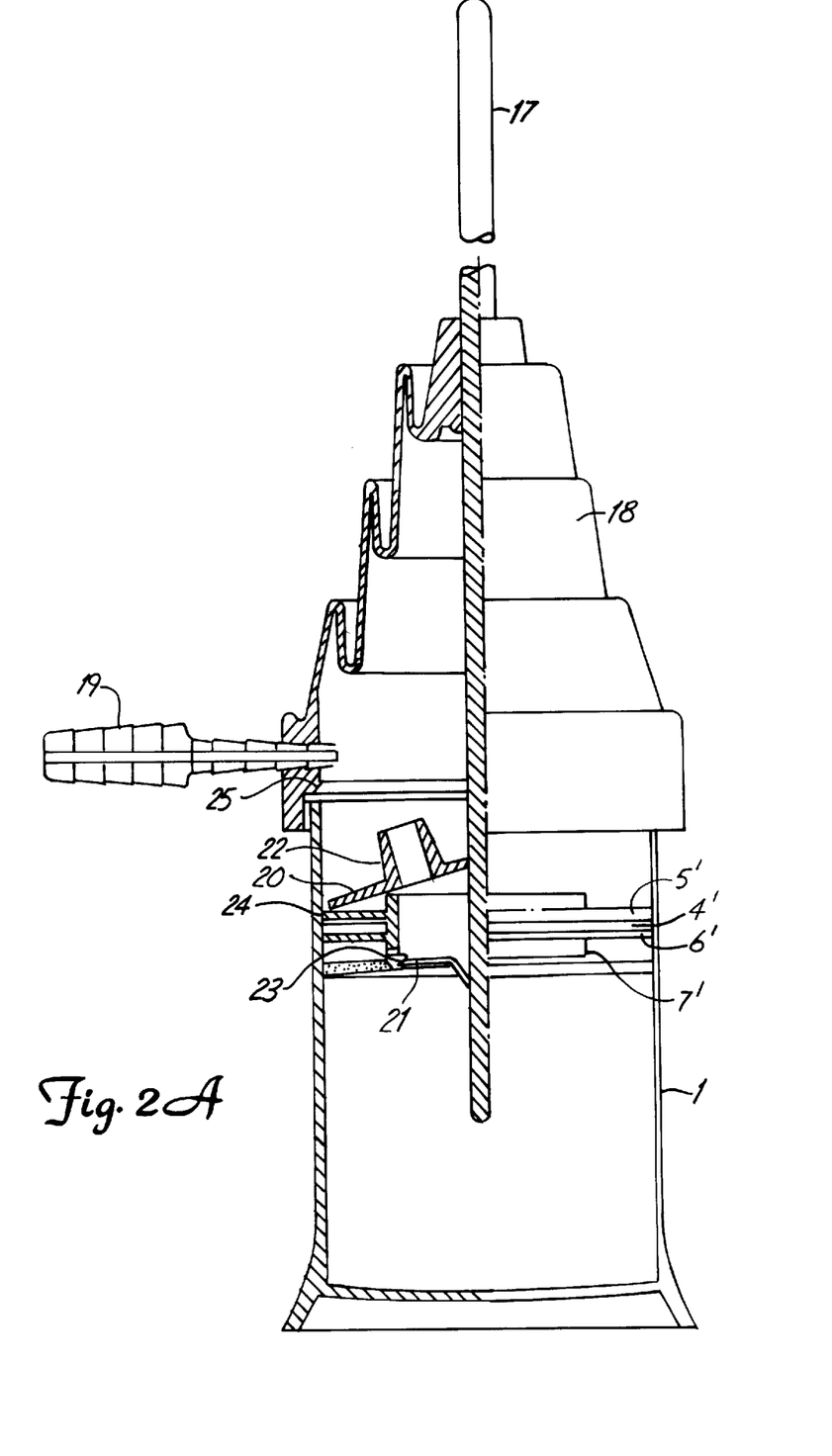
FIG. 2A shows the partial section of FIG. 2, after the inserts have been stripped of the stirring rod and with the stirring rod piercing the filter.

As soon as the lamella 7' of the body 4' fully contacts the polymer powder and has compressed the polymer powder to about two thirds of its original volume in a way similar to that described by means of FIG. 1, the body 4' is withdrawn orthogradely in the axial direction of the vessel 1 by means of the stirring rod 17 inserted into the central insert 20, until the thickening 24 of the lamella 5', which is slightly pre-stressed or biased when being inserted into the vessel 1, engages with the corresponding recess 25 of the vacuum cap 18 above the edge of the vessel 1 to form a press fit. After the engagement of the lamella 5' with the recess 25 of the vacuum cap 18, the stirring rod 17 is tilted and broken out of the body 4' together with the inserts 20 and 22 by breaking the preformed rupture sites. Subsequently, the stirring rod 17 is further withdrawn, whereby the remaining inserts 20 and 22 can be stripped off at one of the inner sleeves or swellings, preferably at the lowest sleeve of the vacuum cap 18 and can remain lying loosely on the lamella 5', which is still engaged with the recess 25. Subsequently, the now freely movable stirring rod 17 can once more be pushed into the depth of the vessel 1 as shown in FIG. 2A and can be used in the known way for mixing the preparation consisting of polymer powder and monomer. As described above, the preparation is mixed at first vigorously and then in laminar layers. During the mixing operation, the vacuum of about 250 mbar relative to atmospheric pressure described above can be increased and a low pressure of 840 to 950 mbar with respect to atmospheric pressure can be generated. When the stirring rod is withdrawn as described above, the vacuum pump can optionally be switched off. The mixture of substances produced by means of the apparatus according to FIG. 2 is completely free of bubbles after the stirring rod is removed and the vacuum pump switched off since even the initial preparation contains only few bubbles due to the early evacuation and since during the entire mixing step, which is carried out under a vacuum, new bubbles cannot form.

Figure 3A:
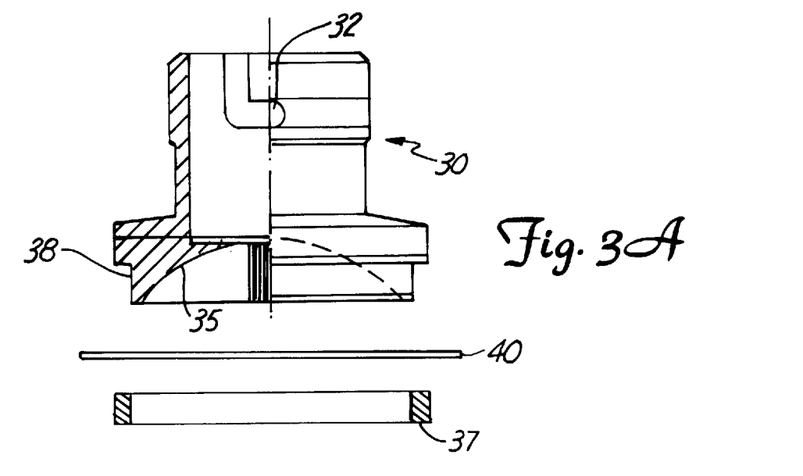
FIG. 3A shows a side view of a partial section of a filter mounting which can optionally be used in the embodiment according to FIG. 1, and an exploded view of a filter and a straining ring.

FIG. 3A depicts a preferred embodiment of a filter mounting 30 having a bayonet catch 32 for taking up a conventional cement cartridge as an extension tube. The filter mounting 30 can for example be put on the cartridge 2 instead of the body 4 in the embodiment according to FIG. 1. As evident in particular from FIG. 3B, the lower surface of the filter mounting 30 facing the bottom of the vessel is provided with ribs having the shape of segments 36 of a circle between which slots 34 are provided which form concave grooves or trenches 35 at the bottom surface of the filter mounting 30. A filter 40 is secured to the bottom surface of the filter mounting 30 by means of a straining ring 37. Reference number 38 designates a supporting area.

Figure 3B:
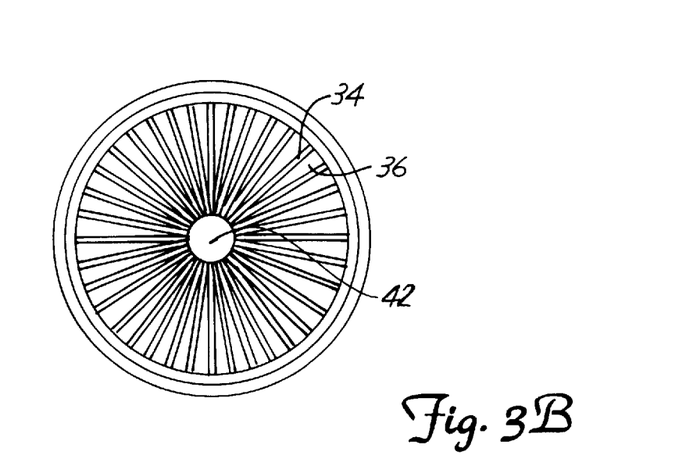
FIG. 3B shows a view of the filter mounting of FIG. 3A from the bottom.

The filter 40 lies plainly on the circle segments 36 on the side of the filter mounting facing the powder. Thus, even thin paper filters can be used as filter 40 and they do not begin breaking despite the suction occurring during the evacuation. On the other hand, due to the concave shape of the grooves 35, the gas flow is favourable, preferably irrotational during the evacuation. Moreover, the gas can also flow through a central through opening 42. In this embodiment, the filter itself provides the sealing with respect to the inner wall of the vessel 1 during the evacuation.

What is claimed is:

1. An apparatus for removing gas inclusions from a preparation of substances to be mixed, said substances comprising at least one liquid component and at least one powder component which projects out of the liquid component, and for subsequently vacuum mixinig the components of the preparation of substances, which apparatus comprises:

an evacuatable mixing vessel having a wall with an inside;

a body which is movable within the mixing vessel, the body having an outer circumference which forms an essentially air-tight seal with the inside of the wall of the mixing vessel, the body having at least one through opening; and a filter covering said through opening, the filter being gas permeable such that occluded gas from the preparation of substances can be sucked off and removed from the powder component through the filter but that the powder component cannot penetrate the filter;

wherein the body is provided with a plain supporting area for the filter and with openings to enable a suction effect via the filter.

2. The apparatus according to claim 1, wherein the body is provided with an inner recess which is dimensioned such that it can optionally receive either the filter or a cartridge, said cartridge being for taking up the mixture of substances.

3. An apparatus for removing gas inclusions from a preparation of substances to be mixed which consists of at least one liquid component and at least one powder component which projects out of the liquid component, and for subsequently vacuum mixing the components of the preparation of substances, which apparatus comprises:

an evacuatable mixing vessel having a wall with an inside;

a body which is movable within the mixing vessel, the body having an outer circumference which forms an essentially air-tight seal with the inside of the wall of the mixing vessel, the body having at least one through opening;

a filter covering said through opening, the filter being gas permeable such that occluded gas can be sucked off and removed from the powder component through the filter but that the powder component cannot penetrate the filter; and a stirring rod for mixing the preparation of substances, wherein the filter is provided such that it can be pierced, by the stirring rod, without parts of the filter falling off.

4. The apparatus according to claim 3, wherein the body is essentially a piston-shaped cylinder, and the filter is placed onto, slipped over, put onto, stretched over, attached to or inserted on the body.

5. The apparatus according to claim 3, wherein the filter is arranged on the side of the body facing the bottom of the vessel.

6. The apparatus according to claim 3, wherein the filter is a filter paper.

7. The apparatus according to claim 6, wherein the filter is a tear-resistant filter paper or crepe paper or a textile filter.

8. The apparatus according to claim 3, wherein the filter is a metal filter.

9. The apparatus according to claim 3, wherein the filter has openings of between 1 and 40 $\mu$m.

10. The apparatus according to claim 3, wherein the body has the shape of a ring about an axis, and wherein the body is axially shiftable in the vessel over the whole length thereof.

11. The apparatus according to claim 3, comprising an adapter means for an evacuating means, the adapter means being on the mixing vessel in fluid communication with the filter to permit suction through the filter during evacuation.

12. The apparatus according to claim 11, further comprising an evacuating means for evacuating the mixing vessel attached on the adapter means.

13. The apparatus of claim 3, wherein all parts of the apparatus are sterilisable and are usable in an operating theatre.

14. The apparatus according to claim 3, wherein the body is essentially a lamellated body, and the filter is placed onto, slipped over, put onto, stretched over, attached to or inserted on the body.

15. The apparatus according to claim 3, wherein the filter has openings of between 1 to 10 $\mu$m.

16. An apparatus for removing gas inclusions from a preparation of substances to be mixed which consists of at least one liquid component and at least one powder component which projects out of the liquid component, and for subsequently vacuum mixing the components of the preparation of substances, which apparatus comprises:

an evacuatable mixing vessel having a wall with an inside;

a body which is movable within the mixing vessel, the body having an outer circumference which forms an essentially air-tight seal with the inside of the wall of the mixing vessel, the body having at least one through opening;

a guiding means detachably attached to the body;

a filter covering said through opening, the filter being gas permeable such that occluded gas can be sucked off and removed from the powder component through the filter but that the powder component cannot penetrate the filter; and a string rod for mixing the preparation of substances, the stirring rod being received in the guiding means such that the stirring rod can be used to move the body along the wall of the mixing vessel, wherein the guiding means is detachable from the outer circumference by tilting of the stirring rod such that the stirring rod is free from the body and can be used to stir the preparation of substances.

17. The apparatus according to claim 16, wherein the filter is attached to the guiding means.

18. An apparatus for removing gas inclusions from a preparation of substances to be mixed, said substances comprising at least one liquid component and at least one powder component which projects out of the liquid component, and for subsequently vacuum mixing the components of the preparation of substances, which apparatus comprises:

an evacuatable mixing vessel having a wall with an inside and a bottom;

a body which is movable within the mixing vessel, wherein the body has an outer circumference with several lamellae, wherein one of the lamellae facing the bottom of the vessel is slightly concave and is porous, the size of the pores being predetermined, and the remaining lamellae form an essentially air-tight seal with respect to the vessel wall, the body having at least one through opening; and a filter covering said through opening, the filter being gas permeable such that occluded gas from the preparation of substances can be sucked off and removed from the powder component through the filter but that the powder component cannot penetrate the filter.

19. The apparatus according to claim 18, wherein the body is provided with an inner ring which supports the filter from rupturing against suction during evacuation, the inner ring having at least one channel defined therein, the channel permitting flow of gas through the filter during evacuation.

20. The apparatus according to claim 18, wherein the filter is provided as a central filter insert attached to the body.

21. A process of removing gas inclusions from a preparation of substances to be mixed which consists of at least one liquid component and at least one powder component, and of subsequently vacuum mixing the components of the preparation of substances in an apparatus which comprises a mixing vessel and a body which is movable within the mixing vessel, said process comprising the steps of:

pouring in the liquid component and adding the powder component such that the powder component projects out of the liquid component;

evacuating the mixing vessel in such a way that the occluded gas is sucked off and removed from the powder component and the powder component is thus compressed without being sucked off the vessel; and mixing the components of the preparation of substances in the evacuated mixing vessel.

22. The process according to claim 21, wherein in the mixing step the components of the mixture of substances are mixed by means of a stirring rod.

23. An apparatus for removing gas inclusions from a preparation of substances to be mixed, said substances comprising at least one liquid component and at least one powder component which projects out of the liquid component, and for subsequently vacuum mixing the components of the preparation of substances, which apparatus comprises:

an evacuatable mixing vessel having a wall with an inside;

a body which is movable within the mixing vessel, the body having an outer circumference which forms an essentially air-tight seal with the inside of the wall of the mixing vessel, the body having at least one through opening; and a filter covering said through opening, the filter being gas permeable such that occluded gas from the preparation of substances can be sucked off and removed from the powder component through the filter but that the powder component cannot penetrate the filter;

wherein the body is provided with a plain supporting area for the filter which supports the filter from rupturing against suction during evacuation and with slots defined in the plain supporting area, the slots being connected to the through opening, the slots enabling a flow of gas through the filter and then in the slots to the through opening during evacuation.

24. An apparatus for removing gas inclusions from a preparation of substances to be mixed which consists of at least one liquid component and at least one powder component which projects out of the liquid component, and for subsequently vacuum mixing the components of the preparation of substances, which apparatus comprises:

an evacuatable mixing vessel having a wall with an inside and a bottom;

a body which is movable within the mixing vessel, the body having an outer circumference which forms an essentially air-tight seal with the inside of the wall of the mixing vessel, the body having at least one through opening;

a guiding means attached at a surface of the body facing away from the bottom of the vessel;

a filter covering said through opening, the filter being gas permeable such that occluded gas can be sucked off and removed from the powder component through the filter but that the powder component cannot penetrate the filter; and a stirring rod for mixing the preparation of substances, the stirring rod being received in the guiding means such that the body is movable back and forward by means of the stirring rod.

* * * * *

UNITED STATES PATENT AND TRADEMARK OFFICE
CERTIFICATE OF CORRECTION

PATENT NO. : 5,857,771
DATED : JANUARY 12, 1999
INVENTOR(S) :
KLAUS DRAENERT

It is certified that error appears in the above-identified patent and that said Letters Patent is hereby corrected as shown below:

On title page, item [54] and Col. 1, line 4, delete "VACCUM", insert --VACUUM--

Col. 7, line 43, delete "mixinig", insert --mixing--

Col. 9, line 7, delete "string", insert --stirring--

Signed and Sealed this

Seventh Day of September, 1999

Attest:

Q. TODD DICKINSON

Attesting Officer       Acting Commissioner of Patents and Trademarks